United States Patent [19]

Eckenhoff et al.

[11] Patent Number: 4,865,845
[45] Date of Patent: Sep. 12, 1989

[54] RELEASE RATE ADJUSTMENT OF OSMOTIC OR DIFFUSIONAL DELIVERY DEVICES

[75] Inventors: James B. Eckenhoff, Los Altos; John Urquhart, Palo Alto, both of Calif.

[73] Assignee: ALZA Corporation, Palo Alto, Calif.

[21] Appl. No.: 90,720

[22] Filed: Aug. 28, 1987

Related U.S. Application Data

[63] Continuation of Ser. No. 842,687, Mar. 21, 1986, abandoned.

[51] Int. Cl.$^4$ .............................................. A61M 31/00
[52] U.S. Cl. ..................................... 424/424; 424/468; 604/892.1
[58] Field of Search ............... 424/422, 424, 468, 471; 604/892.1, 57

[56] References Cited

U.S. PATENT DOCUMENTS

| | | | |
|---|---|---|---|
| 3,760,984 | 9/1973 | Theeuwes | 222/95 |
| 3,845,770 | 11/1974 | Theeuwes et al. | 128/260 |
| 3,916,899 | 11/1975 | Theeuwes et al. | 128/260 |
| 3,987,790 | 10/1976 | Eckenhoff et al. | 128/260 |
| 3,993,058 | 11/1976 | Hoff | 128/130 |
| 3,993,073 | 11/1976 | Zaffaroni | 128/260 |
| 3,995,631 | 12/1976 | Higuchi et al. | 128/260 |
| 4,016,880 | 4/1977 | Theeuwes et al. | 128/260 |
| 4,111,202 | 9/1978 | Theeuwes | 128/260 |
| 4,111,203 | 9/1978 | Theeuwes | 128/260 |
| 4,203,440 | 5/1980 | Theeuwes | 128/260 |
| 4,203,442 | 5/1980 | Michaels | 128/260 |
| 4,210,139 | 7/1980 | Higuchi | 128/260 |
| 4,300,558 | 11/1981 | Eckenhoff et al. | 128/260 |
| 4,304,232 | 12/1981 | Michaels | 604/892.1 |
| 4,320,758 | 3/1982 | Eckenhoff et al. | 128/260 |
| 4,327,725 | 5/1982 | Cortese et al. | 128/260 |
| 4,350,271 | 9/1982 | Eckenhoff | 222/386.5 |
| 4,367,741 | 1/1983 | Michaels | 604/892 |
| 4,474,575 | 10/1984 | Eckenhoff et al. | 604/131 |

Primary Examiner—Nancy A. B. Swisher
Attorney, Agent, or Firm—Edward L. Mandell; Steven F. Stone; Paul L. Sabatine

[57] ABSTRACT

A sleeve shaped structure covers a portion of the transport area of a diffusional or osmotic delivery device. The structure is durable and inert to the use environment. Markings on the structure indicate where breaking or cutting will produce a predictable alteration in delivery rate. Among other attachment means, a water soluble adhesive maintains the structure on the delivery device.

22 Claims, 3 Drawing Sheets

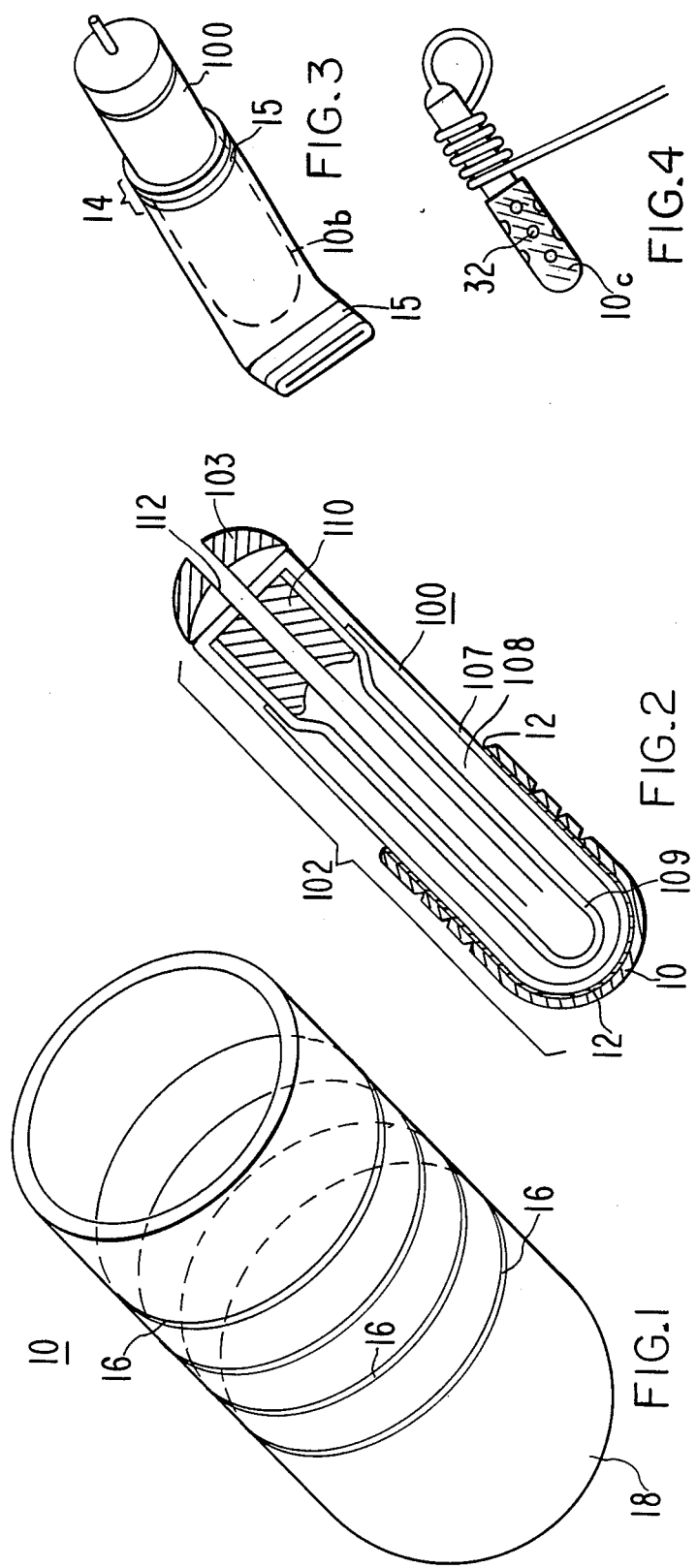

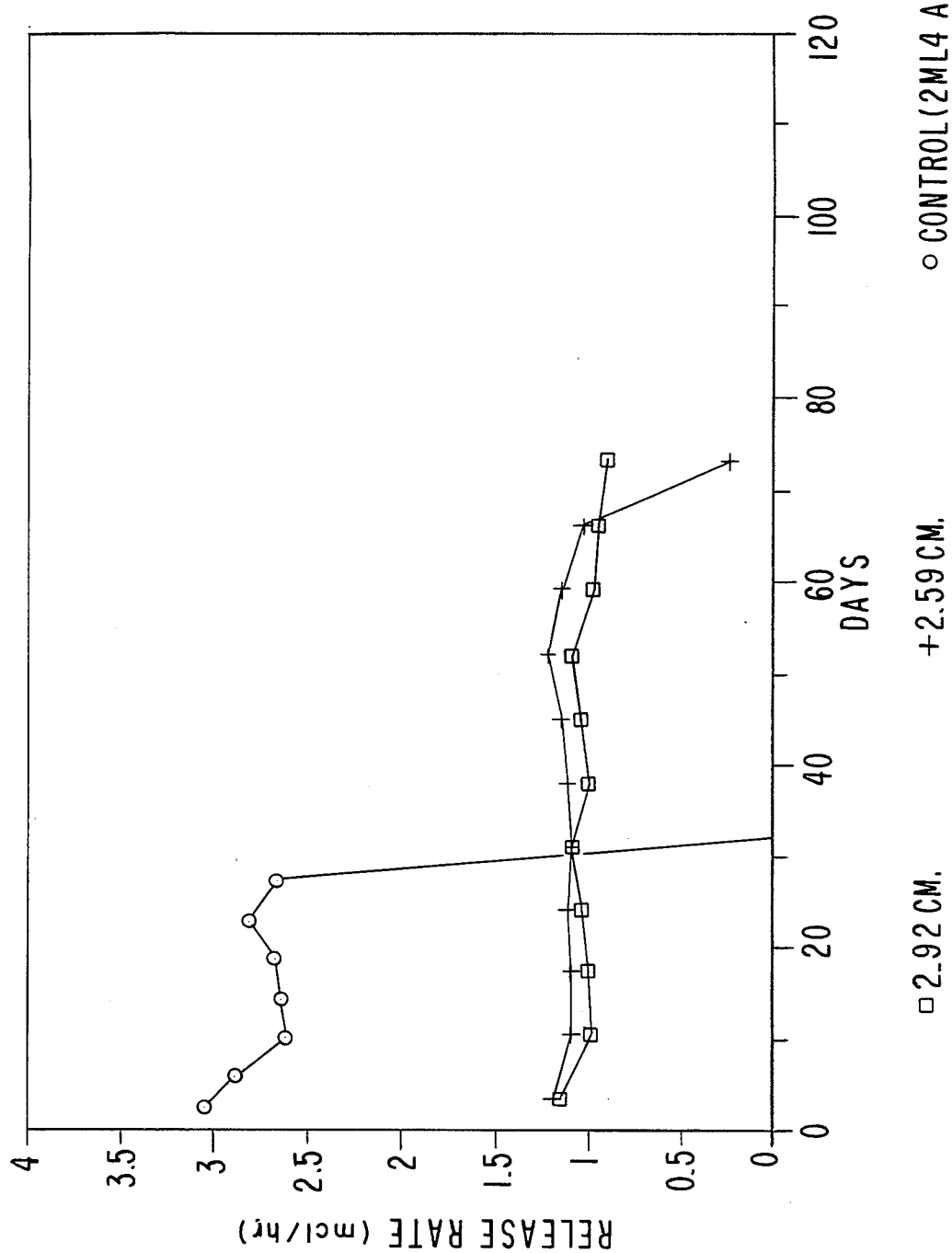

RELEASE RATE ADJUSTMENT OF OSMOTIC OR DIFFUSIONAL DELIVERY DEVICES

RELATED PATENT APPLICATIONS

This application is a continuation of Ser. No. 06/842,687, filed on Mar. 21, 1986 now abandoned.

BACKGROUND OF THE INVENTION

The invention relates to the delivery of substances from devices, and more particularly, to extending the duration of delivery from diffusional or osmotic devices.

Diffusional and osmotic delivery devices are gaining in popularity as a means of delivering substances, usually but not always drugs, into an environment at a well defined rate which is preset in the manufacturing of the device. Currently, these devices are used most extensively to deliver: therapeutic substances to cattle (U.S. Pat. No. 4,300,558); drugs to laboratory animals (U.S. Pat. No. 4,320,758), or fertility-preventing hormones to humans (U.S. Pat. No. 3,993,073). The devices currently exhibiting widespread popularity, however, are limited to fixed delivery rates. Users have become increasingly desirous, however, to have devices of different delivery rates, or delivery rates which they can adjust themselves.

This problem has been addressed in the prior art, however solutions include manufacturing changes, such as: reformulation of the devices with a different concentration or loading of substance; laminating membranes of different permeability in layered contact with the drug formulation layer; or other such non-adjustable formulation changes which predetermine the substance release rate pattern. An inherent problem is that the user must purchase devices with foreknowledge of the delivery rates he or she will require. To avoid delays, the user would then have to maintain a stock of a variety of devices. Additionally, the user is confined to the release rate characteristics manufactured into the delivery device. Accordingly, what must be provided is a means of allowing the user to alter the release rate depending upon the requirements of the intended use. As a result, the user enjoys the greatest flexibility, and need only stock one device.

An approach to the provision of a separate delivery rate adjustable device is found in U.S. Pat. No. 4,474,575. A separate housing encloses the delivery device, wherein the fluid to activate an osmotic delivery device is additionally provided within the housing. Screws threadably move occluding panels into proximity to the delivery device. This device is useful where a separate activating fluid must be provided, as in the intravenous application illustrated in FIG. 6 of that reference. This configuration is complicated, however, where a separate activating environment need not be provided. Moreover, the device has an attendant bulk which is undesirable in many applications. Moreover, the device cannot be implanted within an animal or human body. Removing the housing in applications where it is not needed destroys the adjustability of the device. Additionally, there are added costs associated with a device of this complexity, which should not be borne by users who have no need for a separate activating environment.

Another approach to adjusting the delivery rate downward is to coat the transport area of the delivery device with an impermeable material, where the material will not function as an activating fluid. Specifically, the material must not be able to permeate the transport wall. Accordingly, solvents cannot be used; thus, the material must generally be a solid at use temperatures, and is heated to allow dip-coating of the transport wall. The selection of materials which are suitable is thus limited in that the melting temperature must be low enough to avoid damage to the wall of the device, which typically has a low melting point itself. In the prior art, paraffin wax has been used as the dip-coating, impermeable material. This technique has a number of disadvantages. A threshold concern is that the dip-coating process, and the material itself, may alter the operating characteristics of the device, rendering the predetermination of delivery rates uncertain. Moreover, the material is not suitable for many of the environments in which the device may be placed. Particularly, paraffin is soft, may be incompatible with the environment of use, may become dislodged in movements of the organism, or may be abraded against internal structures, resulting in the release of material into the organism. In laboratory experiments, this is an unacceptable result. In therapy, it is obviously undesirable to introduce unretrievable foreign material. The use of paraffin or a dip-coating process by the user additionally does not guarantee for accurate predictability. In the dipping process, it would be imperative to maintain the device in a perfectly upright position in order to coat to an exact marking. Further, determining the area of the device which must be covered in order to alter its performance by a particular fraction can be difficult if not impossible to accurately determine outside of the manufacturing facility. Therefore the practice of paraffin or any material dip-coating does not provide the user with an accurate means of altering the release characteristics of a delivery device, nor does the method provide a durable, inert, reproducible, or technically safe device.

It is therefore an object of the invention to provide a means and method for enabling the post-manufacture adjustment of the delivery rate of diffusional or osmotic delivery devices.

It is a further object to provide for quick and simple adjustment of devices already manufactured and in the marketplace.

It is yet another object to provide for adjustment whereby the adjustment device is: securely fastened to the delivery device; does not introduce unwanted materials into the use environment; and provides for accurate adjustment of delivery rate change by the user.

SUMMARY OF THE INVENTION

In accomplishing the foregoing and related objects, the invention provides a device which covers a portion of the transport area of osmotic or diffusional delivery devices. Osmotic or diffusional fluid is prevented from reaching the covered or occluded area, and thus the rate at which material is pumped or delivered from the delivery device is reduced.

The device has the general shape of a sleeve, and fits over the transport area of diffusional or osmotic devices. The transport area is that area through which fluid passes to activate the device. For example, the transport area for a diffusional device is across wall 11 of the device described in U.S. Pat. No. 3,993,073, or across wall 23 of U.S. Pat. No. 3,993,058. For osmotic devices, examples of transport area include semipermeable membrane 12 of U.S. Pat. No. 4,320,758, or membrane 12 of U.S. Pat. No. 4,111,202.

The sleeve functions by occluding a portion of the transport surface, thus reducing the contact area to fluids through which (a) substances are released by diffusional mechanisms, or (b) fluid required is imbibed to generate the osmotic pressure for osmotic pumping. It is important that the fluid does not contact the transport area, therefore the sleeve forms a seal at least at each of its ends, with respect to the covered area. The cited devices typically have smooth rounded edges, whereby a common sleeve shape is a cylinder closed at one end, such as a the shape of a test tube.

In accordance with one aspect of the invention, the sleeve provides for accurate predetermination of delivery rates, by occluding a precisely defined portion of the transport area. The sleeve may be sized to change the delivery rate in commonly desired proportions, such as 2×, 3× or 4× the standard delivery duration for the device. Where it is desired to provide the user with a choice of durations, the sleeve is marked or perforated at distinct zones, whereby at least two separate areas are determined. The sleeve is cut or broken off along the perforated zone to provide a sleeve of different size and therefore delivery rate size. To support the sleeve during cutting, a mandrel may be inserted within.

In accordance with yet another aspect of the invention, the sleeve is formed from a biologically inert material which is sterilizable, and is chemically compatible with the environment where it is to operate and the chemicals it is to deliver. In addition, the material is impermeable to the osmotic or diffusional fluid. Typically, a polymer is best, whereby the sleeve is molded, as by injection or extrusion, for example. Materials which may be used include polyethylene; ethylene vinyl; natural rubber; polyamides; polyurethanes; polymethylmethacrylate; polyvinylidene chloride; polyvinyl chloride; styrene acrylonitrile; styrene butadiene; polystyrene; block copolymer; polyolefin; latex rubber; fluoroelastemers; puma; acrylonitrile; polysulfone; alophinics; polyesters and SARAN resin, available from DOW Corning; acrylics, or polyethylene.

In accordance with a further aspect of the invention, the sleeve is attached to the device, whereby diffusional or osmotic fluid is prevented from contacting the covered portion of the transport area. Certain materials may be heat shrunk, such as the polyolefins. Tubing can be placed over the device, and heat shrunk into sealing conformity. The tubing end is then heat sealed shut. Alternatively, an adhesive is used to maintain the sleeve on the delivery device. The adhesive is applied to the transport area, or is disposed in the closed end of the sleeve. A measured amount of adhesive is provided to reduce waste, and avoid coating areas which are not to be occluded. A water permeable adhesive is used, whereby adhesive which has not been wiped off does not interfere with the operations of the delivery device. An example is an adhesive ester, specifically cellulose ester.

The invention is practiced by first sliding a delivery device into the sleeve. The sleeve is attached to the device by heat sealing, adhesion, or other method, such as pressure connectors. Prior to insertion of the device, the sleeve may be cut or broken along the weakened or marked zone to form two portions—a discarded portion, and the attenuated sleeve. A mandrel may be inserted into the sleeve where support is needed, particularly for cutting a rigid sleeve. Alternately, a soft or elastomeric sleeve can be simply cut with scissors.

BRIEF DESCRIPTION OF THE DRAWINGS

Other aspects of the invention will become apparent after considering several illustrative embodiments taken in conjunction with the drawings in which:

FIG. 1 is a perspective view of a device in accordance with the invention;

FIG. 2 is a cross-sectional view of a device in accordance with the invention installed on a delivery device;

FIG. 3 is a perspective view of an alternative device in accordance with the invention installed on a delivery device by heat sealing;

FIG. 4 is a perspective view of another alternative embodiment in accordance with the invention which has a plurality of fenestrae, installed on a delivery device adapted to deliver a pattern of substance through a catheter-like extension;

FIG. 5 is a graph of release rate, or delivery rate, of a delivery device, comparing the device without and with two embodiments in accordance with the invention installed thereon.

DETAILED DESCRIPTION OF THE INVENTION

Figure 6:
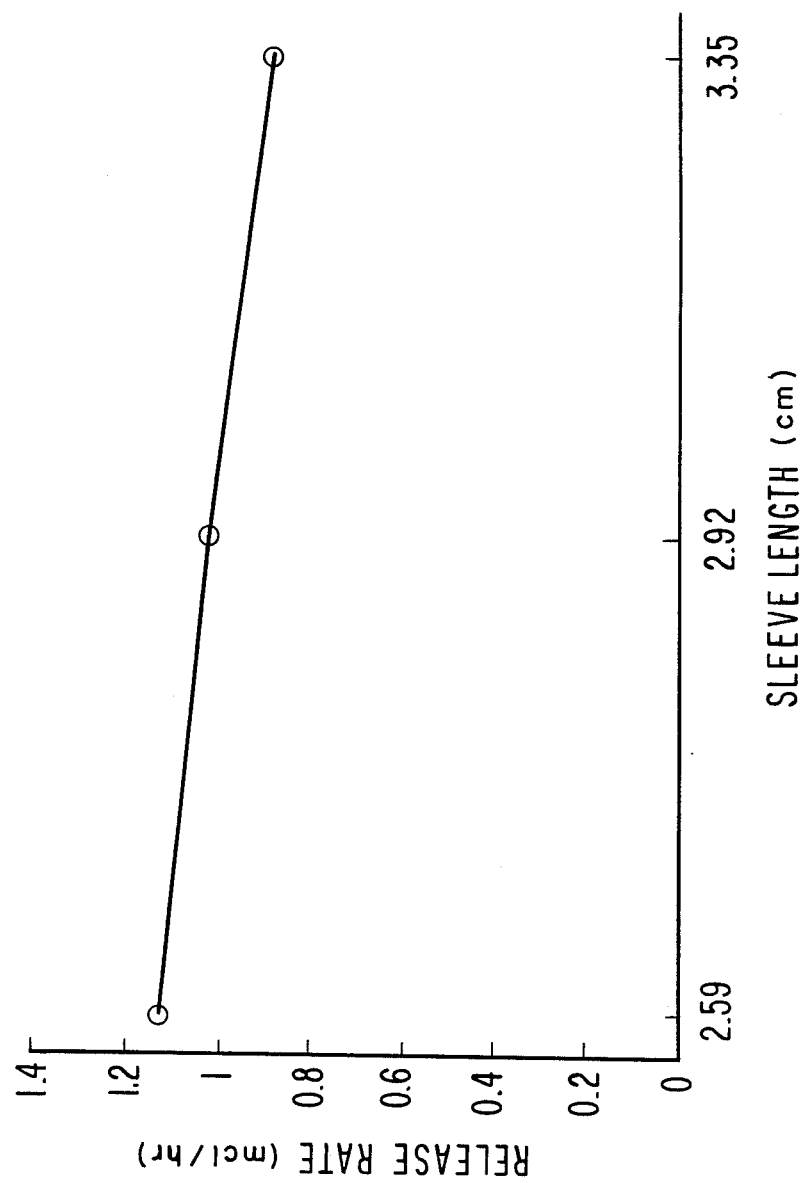
FIG. 6 is a graph illustrating the relationship between covered transport area and release rate, or delivery rate, of a delivery device having a portion of its transport area covered by sleeves in accordance with the invention, of various lengths.

With reference to the figures, a device 10 is sized to fit over an osmotic or diffusional delivery structure, such as fluid imbibing pump 100. The device is attached to the selectively permeable region, or transport area, 102 of pump 100 by an adhesive 12, or by heat shrinking device 10 itself. The device provides an external means of extending the duration of osmotic pump 100 by extrinsically reducing the exposed surface area of portion 102 to the water transport process.

The term "fluid imbibing pump" encompasses that class of delivery devices which deliver their contents, upon exposure to an external fluid, at a rate corresponding to the rate at which the external fluid is imbibed into the pump. These delivery devices are known to the art and operate on diffusional and osmotic principals and are disclosed for example in U.S. Pat. Nos. 4,350,271; 4,327,725; 4,300,558; 4,210,139; 4,203,442; 4,203,440; 4,111,203; 4,111,202; 4,016,880; 3,995,631; 3,987,790; 3,916,899; 3,845,770; and 3,760,984.

The typical osmotic pump includes a semipermeable membrane, i.e., a membrane permeable to an external fluid by impermeable to the solute or the pharmacologically active agent or drug to be dispensed. As the external fluid is imbibed through the semipermeable membrane, the drug solution of formulation is discharged at a controlled rate of delivery through an opening in a suitable housing structure for the osmotic pump. For a more complete discussion, and for a detailed description of the pump 100, shown in the figures, reference may be had to the cited references, particularly U.S. Pat. Nos. 4,300,558; 3,987,790; and 3,845,770.

The specific structure of pump 100 does not in and of itself form a part of this invention and it is contemplated that any pump structure which functions by the controlled imbibition of a fluid from an external source to generate a relative constant internal pressure on a fluid to be dispensed can be used. Preferred embodiments utilize pumps such as disclosed and claimed in the above cited patents. The pumps are inexpensive and available under the trademark ALZET® osmotic pumps from ALZA Corportion, 950 Page Mill Rd., Palo Alta, CA. An ALZET osmotic pump comprises a rigid semipermeable membrane 107 which is preferably formed of cellulose acetate, surrounding an osmotically effective solute 108, preferably salt and an impermeable flexible rubber bag 109 preferably formed from styrene butadiene block coplymer. A plug 110 formed of the same material as bag 109 is provided with a central port which is friction fitted around a blunted standard hypodermic needle 112 which is carried on the end of fitting 103. The gauge of the needle is selected to provide the proper orifice diameter and acts as the flow conduit for the pump.

Hereinafter, Device 10 will be referred to as sleeve 10, in order to be more descriptive. It should be understood however that the configuration of devices in accordance with the invention are not limited to definitions of "sleeve". With reference to FIG. 1, sleeve 10 is sized to closely conform to membrane 107. The inside diameter of sleeve 10 is therefore approximately equal to the outside diameter of pump 100, depending on the flexibility of the sleeve. In a preferred embodiment, sleeve 10 has the form of a single closed ended cylinder. Sleeve 10 length is determined by the desired final delivery characteristics, as discussed further below. In accordance with one embodiment, sleeve 10 is scored to enable quick and simple changes in length, with high precision.

Generally, it is desired to prevent external activation liquid from contacting a portion of membrane 107. In accordance with the invention, this may be achieved by the form-fitting sleeve shown in FIG. 1, or by an oversized but continuous sleeve 10b, shown in FIG. 3, which is attached by heat sealing 15 or adhesive to sleeve 100 at a neck 14. Alternatively, a sleeve 10c is provided with fenestrae, or apertures 32, sized to provide predictable modifications in the delivery rate of a particular pump, as can be seen in FIG. 4. Prolonged pulse delivery is achieved with the use of the structure shown in FIG. 4.

Sleeves 10, 10b, and 10c may be molded, as by extrusion or injection. Score lines 16 may be produced in the mold or in a latter step. The sleeve length is adjusted by breaking or cutting off the additional length at the score. For particular materials, a mandrel can be provided which is inserted within the sleeve. A knife can then be used to cut the sleeve, guided either by markings on the sleeve, or, where the sleeve is clear, markings on the mandrel. Where it is known what delay period is desired, pump 100 may be provided with sleeve 10 installed in the factory. Other methods for producing parts as described herein, from the materials described below, may be used to produce pumps in accordance with the invention.

Sleeves in accordance with the invention may be fabricated from materials which are biologically inert to the target organism, and chemically compatible with the pump, its materials and the delivered substance. Examples include SARAN resin, available from Dow Corning; styrene butadiene; block copolymer; polyolefin; latex rubber; fluoroelastemers; puma; polymethylmethacrylate; acrylonitrile; polysulfone; alophinics; ethylene vinyl; natural rubber; polyamides; polyvinyl chloride; polyvinylidene chloride; polyurethanes; styrene acrylonitrile; polystyrene; puma; polyesters; acrylics; and polyethylene. Generally, these materials possess the additional features of moldability and sterilizability. Sterilizing may be performed by chemicals or radiation, and in some cases, by autoclaving.

To adhere sleeve 10 to pump 100, an adhesive is placed in the bottom end 18, and the pump is inserted into the sleeve. Displaced adhesive flows upward, filling the gap between membrane 107 and the inner surface of sleeve 10. Excess adhesive is wiped off. To minimize excess, adhesive is provided in premeasured aliquots, which correspond to various sleeve lengths. An appropriate adhesive is cellulose ester at a 20% concentration in acetone solvent. The dried adhesive has a high permeability to water, a common external activating fluid. Accordingly, excess adhesive around exposed membrane surface area is not detrimental to the operation of pump 100 to any significant degree. Other adhesives which are water permeable when dry, and are biologically and chemically compatible, while exhibiting sufficient strength, may be used in accordance with the invention.

Performance characteristics of a pump 100 with sleeve 10 installed may be accurately determined. The pumping rate Q of pump 100 is defined by the equation:

$$Q = A/T * K \Delta \pi$$

where A is the surface area for the water transport process, T is the membrane thickness, and $K \Delta \pi$ is the water transmission rate constant for the membrane. By reducing A through increasing the height of the impermeable sleeve the pumping rate can be lowered, hence extending the useful lifetime. The equation that will predict the modified pumping rate, Qm, from a system having a design pumping rate of Qd will be $Qm = Qd * (1 - H/h)$ where H is the height of the impermeable sleeve and h is the overall height of the cylindrical section of the semipermeable membrane a monotonically declining relationship is observed if release valve from the osmotic pump is plotted as a function of increasing height of the impermeable sleeve, as can be seen in FIG. 6.

EXAMPLE A

A sleeve 10 is fabricated as follows: Polymethylmethacrylate V811 was dried in an oven at 60 degrees C to remove residual water. A model 200 Arburg injection molding machine was set to the following conditions after installing the osmotic pump impermeable sleeve mold:
  clamp set —30 sec
  injection time —10 sec
  back pressure —5 psi
  barrel temp —220 degrees C
  nozzle temp —425 degrees C
  mold temp —½ degrees C
Sleeves of 0.065 cm wall thickness and outside lengths of 2.59 cm and 2.92 cm were produced and washed in a 30% aqueous solution of ethanol. Osmotic pumps of 2 milliliters fill volume and volumetric pumping rate, 2.73×/—0.12 microliters per hour were installed into the sleeves in the following manner. A glue solution was formulated of cellulose acetate 398-10 in a binary solvent system of acetone and ethanol (90:10): the weight composition of cellulose acetate 398-10 was 20% in the solvent system. Approximately 100 microliters of the glue solution was injected into the bottom of the sleeve and the excess glue solution was wiped off. The systems were dried under room air, room temperature conditions for 16 hours and then dried at 50 degrees C for 48 hours.

EXAMPLE B

In Vitro release rate tests of the sleeves of EXAMPLE A, and control pumps without sleeves, were performed in isotonic saline at 37 degrees C. FIG. 5 illustrates the pumping rates from these delivery devices, which delivered FD&C Blue No. 1 dye solution. FIG. 6 illustrates the monotonically delivering steady state pumping rate versus increasing length of impermeable sleeves 10. It can be extrapolated that a pump of 4 weeks duration without sleeve 10 can be caused to pump for 100 days with a sleeve 10 of length 3.35 cm.

It can be seen from FIG. 5 that a direct correlation exists between the surface area occluded by sleeve 10 and pumping rate. Accordingly, the invention provides a simple means of lowering the pumping rate and therefore extending the duration of these popular delivery device structures. Notches, or markings on sleeve 10 can provide guidance to an investigator in predetermining the pumping duration. Accordingly, the uncertainty of prior art methods are avoided. Moreover, handling problems are alleviated. Sterility is established in the factory, and is easily maintained in the lab during installation and use. The predictability provided by the invention opens new research avenues. Now investigators can conduct long term studies without subjecting test animals to repeated trauma relating to pump replacement. Further, the invention provides a useful medical device. The therapeutic dosage for humans and animals can be adjusted and maintained over longer time periods, resulting in greater convenience and patient compliance. While various aspects of the invention have been set forth by the drawings and the specification, it is to be understood that the foregoing description is for illustration only and that various changes in parts, as well as the substitution of equivalent constituents for those shown and described, may be made without departing from the spirit and scope of the invention as set forth in the appended claims.

What is claimed is:

1. A device for increasing and delivering duration of an osmotic or diffusional delivery device of a predetermined configuration, said delivery device having an external surface which acts as a transport area through which fluid passes to activate said delivery device, comprising:
   a preformed integral sleeve impermeable to the passage of fluid, having a configuration substantially similar to said external surface and adapted to cover a portion of said surface;
   whereby osmotic or diffusional fluid is prevented from contacting the covered portion; and
   a means for precisely controlling the portion of transport area covered by said sleeve comprising markings on said sleeve having at least one weakened zone.

2. The device of claim 1 which further comprises:
   a means for adjusting the size of said sleeve.

3. The device of claim 2 wherein said means for adjusting comprises at least one score line disposed about said sleeve.

4. The device of claim 1 wherein said sleeve comprises a plurality of weakened zones each having a predetermined relationship to the delivering duration of said osmotic or diffusional device.

5. The device of claim 1 which further comprises:
   a means for attaching said sleeve to the delivery device.

6. The device of claim 5 wherein said means for attaching comprises a fluid permeable adhesive.

7. The device of claim 6 wherein said adhesive contains an ester.

8. The device of claim 6 wherein said adhesive is at least as fluid permeable as the transport area.

9. The device of claim 7 wherein said adhesive contains cellulose ester.

10. The device of claim 1 wherein said sleeve has the form of a cylinder, closed at one end.

11. The device of claim 1 wherein said sleeve is formed from polymethylmethacrylate, which is impermeable to said osmotic or diffusional fluid.

12. The device of claim 1 wherein said sleeve is formed from a styrene butadiene block copolymer, which is impermeable to said osmotic or diffusional fluid.

13. The device of claim 1 wherein said sleeve is formed from polysulfone, which is impermeable to said osmotic or diffusional fluid.

14. The device of claim 1 wherein said sleeve is formed from polycarbonate, which is impermeable to said osmotic or diffusional fluid.

15. The device of claim 1 wherein said sleeve is formed from polyethylene, which is impermeable to said osmotic or diffusional fluid.

16. A method of prolonging the delivering rate of diffusional or osmotic delivery devices of a predetermined configuration having an external surface which acts as a transport area through which fluid passes to activate said device, for a predetermined length of time, comprising the steps of:
   forming a sleeve impermeable to the passage of fluid, sized to cover a portion of the transport area and having at least one weakened zone;
   removing a portion of the sleeve at said weakened zone;
   inserting the delivery device into the sleeve; and
   attaching the sleeve to the delivery device;
   wherein the assemblage thus formed is exposed to the osmotic or diffusional fluid to commence delivering.

17. The method of claim 16 wherein said forming step further comprises:
   forming a sleeve comprised of a plurality of weakened zones each having a predetermined relationship to the delivering duration of said osmotic or diffusional device.

18. The method of claim 16 wherein said attaching step further comprises:
   disposing a measured amount of a fluid permeable adhesive in the sleeve.

19. The method of claim 16 wherein said attaching step further comprises:
   disposing a measured amount of a fluid permeable adhesive on the transport area.

20. The method of claim 16 which further comprises the steps of:
   inserting a supporting mandrel into the sleeve; and
   cutting the sleeve along the weakened zone.

21. The method of claim 16 which further comprises the step of:
   marking the sleeve to determine at least two separate portions.

22. The method of claim 21 which further comprises the steps of:
   inserting a supporting mandrel into the sleeve; and
   cutting the sleeve along the marked zone.

* * * * *

UNITED STATES PATENT AND TRADEMARK OFFICE
CERTIFICATE OF CORRECTION

PATENT NO. : 4,865,845

DATED : September 12, 1989

INVENTOR(S) : Eckenhoff et al.

It is certified that error appears in the above-identified patent and that said Letters Patent is hereby corrected as shown below:

On column 7, line 43, delete "and" and insert --the--.

Signed and Sealed this

Seventeenth Day of July, 1990

Attest:

HARRY F. MANBECK, JR.

*Attesting Officer*　　*Commissioner of Patents and Trademarks*